US012533460B2

(12) United States Patent
Hagen et al.

(10) Patent No.: US 12,533,460 B2
(45) Date of Patent: Jan. 27, 2026

(54) ENEMA DEVICE, AND A DELIVERY CONTAINER FOR USE IN SAID ENEMA DEVICE

(71) Applicant: Qufora A/S, Allerød (DK)

(72) Inventors: Thit Rose Hagen, Roskilde (DK); Birthe Vestbo Andersen, Graested (DK); Ana Latorre Duque, Alcorisa (ES)

(73) Assignee: Qufora A/S, Allerød (DK)

( * ) Notice: Subject to any disclaimer, the term of this patent is extended or adjusted under 35 U.S.C. 154(b) by 0 days.

(21) Appl. No.: 18/648,818

(22) Filed: Apr. 29, 2024

(65) Prior Publication Data

US 2024/0269370 A1 Aug. 15, 2024

Related U.S. Application Data

(60) Division of application No. 17/725,057, filed on Apr. 20, 2022, now Pat. No. 11,975,163, which is a (Continued)

(30) Foreign Application Priority Data

Oct. 3, 2018 (DK) ............................ PA 201870651

(51) Int. Cl.
*A61M 3/02* (2006.01)

(52) U.S. Cl.
CPC ........ *A61M 3/0245* (2013.01); *A61M 3/0262* (2013.01)

(58) Field of Classification Search
CPC . A61M 3/0262; A61M 3/0245; A61M 3/0254
See application file for complete search history.

(56) References Cited

U.S. PATENT DOCUMENTS

| | | | | |
|---|---|---|---|---|
| 3,844,284 A * | 10/1974 | Schoenfeld | A61M 3/0262 | 604/911 |
| 4,168,032 A * | 9/1979 | Sneider | B05B 11/047 | 222/215 |

(Continued)

FOREIGN PATENT DOCUMENTS

| | | |
|---|---|---|
| CN | 201832276 | 5/2011 |
| CN | 203355001 | 12/2013 |

(Continued)

OTHER PUBLICATIONS

International Search Report and Written Opinion Appl. No. PCT/DK2019/050291, mailed Jan. 3, 2020 (10 pages).

(Continued)

*Primary Examiner* — Tasnim Mehjabin Ahmed
(74) *Attorney, Agent, or Firm* — Fox Rothschild LLP

(57) ABSTRACT

The present invention relates to an enema device comprising a delivery container arranged for accommodating an enema and an applicator nozzle for dispersing the enema, and wherein the delivery container is arranged as a hand held pump and for remaining in an at least partly compressed configuration when the user releases the pressure on said delivery container during use. Thereby is provided a simple, inexpensive and essentially maintenance free enema device which can be used for self-administrating of an enema.

23 Claims, 7 Drawing Sheets

Figure 1:
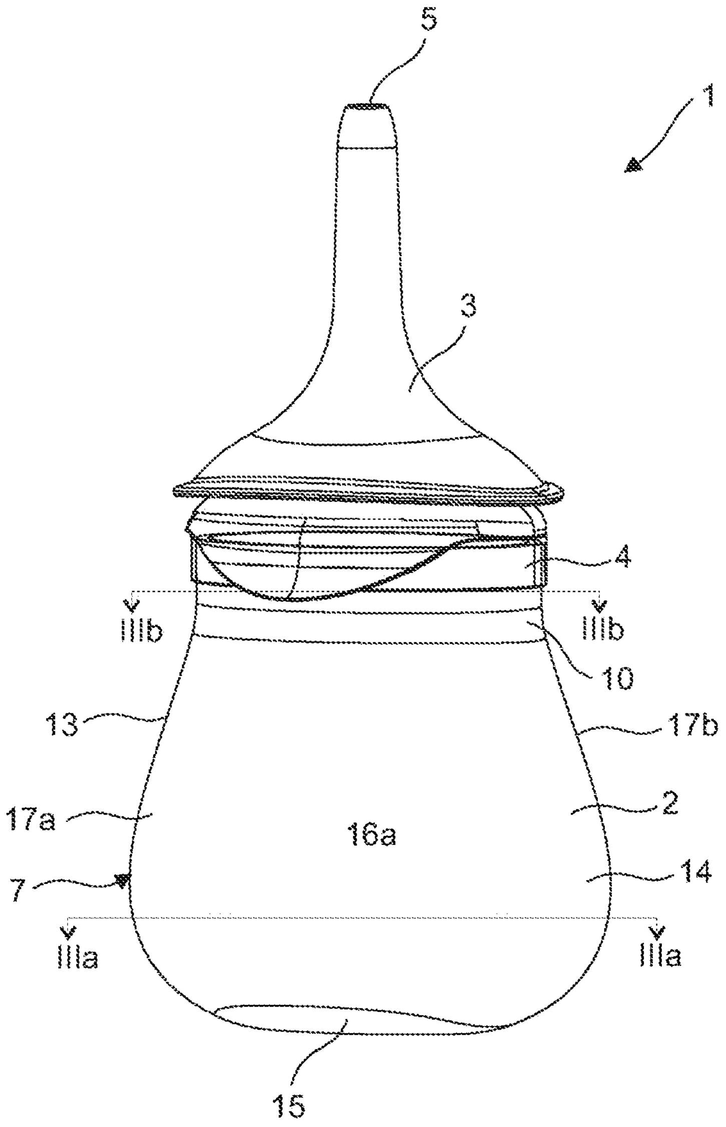

Related U.S. Application Data continuation of application No. 17/281,960, filed as application No. PCT/DK2019/050291 on Oct. 2, 2019, now Pat. No. 11,338,080.

(56) References Cited

U.S. PATENT DOCUMENTS

| | | | | |
|---|---|---|---|---|
| 5,848,993 | A | 12/1998 | Tanhehco et al. | |
| 6,290,108 | B1 | 9/2001 | Gross | |
| 11,338,080 | B2 | 5/2022 | Hagen et al. | |
| 2005/0121408 | A1 | 6/2005 | Deemer et al. | |
| 2007/0005025 | A1* | 1/2007 | Cox | A61M 31/00 604/245 |
| 2008/0029086 | A1* | 2/2008 | Harlan | A61H 35/04 128/200.22 |
| 2017/0007759 | A1 | 1/2017 | Castropil Logarzo | |

FOREIGN PATENT DOCUMENTS

| | | |
|---|---|---|
| CN | 205007273 | 2/2016 |
| GB | 255778 | 7/1926 |
| GB | 2555778 | 5/2018 |
| WO | 2015/123742 | 8/2015 |
| WO | 2018/032102 | 2/2018 |
| WO | 2019/001674 | 1/2019 |

OTHER PUBLICATIONS

International Preliminary Report on Patentability (IPRP), Appl. No PCT/DK2019/050291, mailed Oct. 2, 2020 (15 pages).

* cited by examiner

ENEMA DEVICE, AND A DELIVERY CONTAINER FOR USE IN SAID ENEMA DEVICE

CROSS-REFERENCES TO RELATED APPLICATIONS

This Application is a divisional of U.S. patent application Ser. No. 17/725,057, filed Apr. 20, 2022, which is a continuation of U.S. patent application Ser. No. 17/281,960, filed Mar. 31, 2021, which is a U.S. National Phase of International Patent Application No. PCT/DK2019/050291, filed Oct. 2, 2019, and claims priority to Danish Patent Application No. PA 201870651, filed Oct. 3, 2018. The entire contents of these applications are incorporated herein by reference in their entirety.

The present invention relates to an enema device comprising a flexible delivery container and an applicator nozzle.

Administrating an enema is a common medical procedure whereby fluid is injected into the rectum and lower intestine of a patient in order to induce bowel movement. The need for such a procedure typically arises in patients suffering from certain physical ailments in which voluntary bowel control is impaired or when the bowel needs to be cleaned before e.g. a coloscopy or a surgical operation.

Medical equipment currently exists in the art for administering an enema to patients in need of this procedure. At least one type of equipment consists of an enema squeeze bottle filled with the fluid intended to induce bowel movement, which is capped by a short applicator nozzle to be inserted into the patient's rectum. The applicator nozzle of this type of conventional enema application device often causes discomfort and irritation when being inserted.

Furthermore, the force required to squeeze the liquid from an enema dispenser affects the ease with which a user may administer the liquid. The self-administration a of conventional enema may be especially difficult for patients have poor dexterity, e.g. due to the squeeze force required to deliver a complete dose of the enema liquid.

Although it would be advantageous to decrease the amount of squeeze force required to administer an enema, such a modification may adversely affect other desirable features of the device. In particular, it is desirable to prevent any reflux of liquid back into the delivery container after the enema liquid has been delivered, and it is desirable to prevent leakage of the enema liquid from the dispenser prior to use. A simple reduction in the resistance to flow of the liquid through the device may compromise these features.

Moreover, enemas are often administered to a patient at home when the need for medical assistance does not necessitate a doctor or another health care assistant.

However, it is often difficult for the patient to administer the enema to him or herself since the applicator nozzle not only must be inserted into a sensitive area, but the administration position is also inconvenient for the user making it is difficult for the patient to administer the liquid while steadily holding the enema in the required area. Often the patient is assisted by another individual; however, assistance may not always be available, if, for instance, the patient lives alone. Thus, there is also a need for an enema device that can be effectively self-administered.

Such an enema device is e.g. known from WO2010122537, disclosing a device which can be used for administrating an enema. Said enema device ensures that uncontrolled flow of liquid into or out of the device is prevented by using two one-way valves, one for delivering the liquid and one for refilling the device.

The enema is administered by squeezing the delivery container, and after releasing the compression force, the container may either be re-inflated by drawing surrounding air into the container via a first one-way valve, or the container may be re-loaded with enema by drawing enema into the container via said one-way valve.

The latter will ensure that the device can be used for several administrations as needed by the user, however studies and user feed-back have shown that most user can not get a convenient grip on the delivery container, nor does they not have the strength to provide a constant pressure on the delivery container. Accordingly, the user will first administer a small amount of enema, then release the pressure on said container and after a short period administering a further small amount of enema. However, when pressure is released on the delivery container, air will unintentionally be drawn into the container and mixed with the enema. Air will then be delivered to the colon when the next dosage of enema is administered. This will cause uncomfortable distending of the colon causing pain and cramps. Thus, in order to avoid intake of air, the user will have to apply a constant pressure to the delivery container during the administrating procedure, which may be difficult for users/patients having weak fingers, e.g. due to arthritis or the like.

Furthermore, as air is drawn into the container, expelling of the enema becomes increasingly more difficult. Due to density differences between air and the enema, the device has to be oriented in prevent correctly, order to or reduce administration of air. However, ensuring such an orientation is almost impossible as the enema often is administered on the toilet or in the bed, where the user's/patient's position prevents such an orientation.

Since administration of air will cause discomfort several reloadings of the container with enema are often required in order to deliver an effective dosage of enema and at the same time prevent delivery of air. However, reloading of the container requires easy access to the enema. If the enema for instance is tap water, a user sitting on the toilet, may use the sink as an enema reservoir, however, often the toilet and the sink are to far apart for this to be manageable. Thus, the user has to have a reservoir of enema nearby in order to provide easy reloading, making the reloading both difficult and troublesome.

Thus, there is a demand for a new enema device, which is simple and easy to use and which solves the limitations and disadvantages of the prior art.

It is therefore a first aspect of the present invention to provide a handheld enema device that safely and effectively can administer an enema to a patient without causing discomfort.

It is a second aspect of the present invention to provide an enema device where the liquid is easier to administer, and where air effectively is prevented from being mixed with the enema.

It is a third aspect of the present invention to provide an enema device in which an effective dosage of enema can be administered without required reloading of the delivery container.

It is a fourth aspect of the present invention to provide an enema device that prevents reflux of liquid into the container after use and/or prevents leakage of the fluid prior to use.

In a fifth aspect according to the present invention is provided an enema device that is inexpensive to manufacture and is simple and reliable to use.

In a sixth aspect according to the present invention is provided an enema device that is relatively small and easy to operate, especially by one hand.

In a seventh aspect according to the present invention is provided an enema device arranged to delivery an enema to a patient sitting on the toilet, without requiring reloading with enema.

The novel and unique whereby these and further aspects are achieved is the fact that the enema device according to the present invention comprises a flexible delivery container arranged for accommodating an enema, and an applicator nozzle for dispersing the enema, and wherein the delivery container is arranged as a hand held pump and wherein a cross-section of said delivery container has the shape of an oval, and wherein the delivery container comprises one or more compression zones, arranged for providing a controlled compression said delivery container.

Since the delivery container has a substantially oval cross-section, taken in a horizontal plane when the container is placed in a position of use, it is easier for the user to apply pressure to the sides of the delivery container. In contrast to a delivery container having a circular cross-section, a user will intuitively place/rest the delivery container according to the invention in a specific orientation in the users palm, allowing the user to compress the container by applying pressure to the two longer curved sides of the delivery container using both the finger and the palm, e.g. the thenar muscles at the base of the thumb. This will not only ensure a pleasant and comforting fit in the hand but will also reduce the necessary force needed to compress the container as well as reducing any awkward postures.

Thereby is provided a simple, inexpensive and essentially maintenance free enema device which can be used for administrating enema, and wherein it is the delivery container itself which functions as a pump, i.e. the enema is expelled with the user applies pressure to the sides of the pump, i.e. the delivery container is arranged as a hand held pump. Accordingly the enema device according to the invention can be operated without any external pumping means, making said enema device according small and compact, i.e. the enema device take up as little spatial space or volume as possible, not only ensuring that the device can be handheld and easily operated e.g. with a single hand, but also that the enema device easily can be fitted into a bag or the like.

In a preferred embodiment the delivery container comprises a bottom section with a first cross-section in the shape of an oval, and a top section with a second cross-section in the shape of an oval, and wherein the minor and/or the major axis of the first cross-section is larger than the minor and/or the major axis of the second cross-section. In order to provide a user friendly delivery container, it is preferred that the bottom section tapers towards the top section, i.e. that a smooth transition between the two sections is provided. It is accordingly preferred that the delivery container is shaped as an elongated bulb, both assisting in ensuring that the user can apply pressure to the sides of the container and that a comfortable feel in the hand is provided. Accordingly, the enema device according to the present invention provides an easy expelling of enema without compromising the structural features of the device. The device may in a preferred embodiment have a substantially flat base, such that the delivery container may stand upright e.g. during and/or after filling said container with enema, as this effectively will prevent spilling of the enema.

It is preferred that the delivery container will have a cross-section in the shape of an oval irrespectively of where said cross-section is made in the delivery container, i.e. the oval shape continues in the complete height of the delivery container. The oval may be any kind of oval, it is however preferred that the oval can be clearly distinguished from a circle, as the inventors of the present invention has found that users experience difficulties with applying pressure to a delivery container having a cross-section in the form of a circle, e.g. that the users cannot expel an effective dosage of enema with such containers. Accordingly, the ratio of the minor axis to the major axis of said oval is ⅔ or lower, i.e. if the major axis is 3 cm, then the minor axis is 2 cm or lower, if the major axis is 4.5 cm, then the minor axis is not more than 3 cm, etc.

Even though it is preferred that the oval of the first and second cross-section are identical in shape (even though they have different sizes), said ovals may also have different shapes. It is however preferred that the size and dimensions of the ovals of the respective cross-sections are selected such that the resultant elongated bulb-shaped delivery container is arranged for resting firmly in the hand of the user, and that the user intuitively will hold the delivery container in a cupped hand, allowing the user to apply pressure to the two longer sides of said container using the palm and fingers. A person skilled in the art will understand that the use may apply pressure to the delivery container in any desired way, however, the oval-shaped bulb container may ensure that the user will place the container in a cupped hand.

In a preferred embodiment, the enema device comprises a non-return valve, such that when the patient/user released the compression force on the delivery container, the first non-return valve will effectively prevent backflow of fluid, e.g. air, liquid and faeces from the colon and/or rectum into the enema device. Accordingly, any contamination of the delivery container and it's remaining content, which may occur during and/or after administration of the enema to a patient is precluded.

The non-return valve may e.g. be placed in the applicator nozzle, e.g. at or near an outlet on said nozzle. This may e.g. be preferred if the applicator nozzle is reused, otherwise it will be a less expensive solution to place the non-return valve in the enema device according to the invention.

Such non-return valves are well known in the art, and may be any valve capable of providing the desired properties, e.g. prevent intake of air/fluid etc. to the enema device according to the invention e.g. swing valves, ball valves, diaphragm valves, butterfly valves, and the like.

The non-return valve further has the advantage, that if the user during the administration procedure releases the compression force on the container, air will be prevented from being drawn into the delivery container. Accordingly, air cannot be administered into the patients colon and unnecessary discomfort caused by distending of the colon by air, is effectively prevented.

Furthermore, when the enema is during expelled the administration procedure, the delivery container will collapse, and since the non-return valve will prevent any intake of e.g. air into the container, the delivery container will remain in a collapsed state, even if the user releases the pressure on said container. This ensures that user easily can expel the remaining content from the delivery container, by alternating applying pressure and releasing said pressure from the container, until the desired dosage or the entire enema content has been expelled from the enema device. As the delivery container collapses when the enema is expelled, the user can furthermore easily fell when the enema has been expelled thereby providing a simple indication to the user, when the desired e.g. entire dosage of enema has been administered, i.e. when the delivery container is in a complete or substantially complete compressed condition.

In order to obtain said advantage, it is preferred that the enema device according to the invention does not comprise any means for drawing air and/or fluid into the delivery container during the administration procedure.

The delivery container is arranged as a hand held pump and may accordingly be made of a resilient deformable material with a memory, e.g. silicone, a thermoplastic polymer, polyurethane, polyvinyl-chloride, or a similar soft polymer. This means that the user can apply pressure on the delivery container, whereby the container will collapse and enema is forced out though the applicator nozzle attached to the enema device.

In order to provide a controlled compression of the delivery container, said container comprises one or more compression zones. The compression zones may further be arranged for ensuring that when a compression force is applied to the delivery container, said container will collapse/compress in such a way that substantially the entire content of the enema device is expelled.

Within the context of the present invention, the term "compression zone" means an area/section of the delivery container having a different design/construction/configuration than the remainder of said container.

The compressions zones may be provided in a number of different manners. It is in this respect preferred that the compression zones constitutes a minor portion of the delivery container, and preferably less than 50% of the surface area of the delivery container, preferably less than 30% of said surface area, thereby providing a controlled compression of said container.

In one embodiment the compression zones may be provided by adjusting the wall thickness of the delivery container in one or more compression areas, such that in areas where a large compression force is desired, e.g. at the bottom of the delivery container, the wall thickness of said container is larger than in areas e.g. at the sides of said container, where is lower compression force is desired. In a preferred embodiment, the bottom section of the delivery container will have a larger compression force, and accordingly a larger wall thickness, than the two small sides of the delivery container. Furthermore, the two longer sides of said container will have an even smaller compression force, than the two small sides, and accordingly a small wall thickness. In this way it is ensured that when the user applies pressure to the delivery container, said container will tend to collapse more at the longer sides, etc, thereby providing a controlled collapse. The compression areas may be one or more surface of the delivery container, but may in an preferred embodiment be one or more limited areas of said container, e.g. two opposing circular areas on the two longer sides of the delivery container and/or two opposing circular areas on the two smaller sides of the delivery container, and/or a single circular area at the bottom of the delivery container. In a different embodiment one or more of said compression areas may further be arranged for not compressing/collapsing/bending, even when a large compression force is applied to said area, whereby it is possible to adjust/control the compression of the delivery container even further.

Instead of altering the wall thickness of the delivery container at certain compression areas, the compression zones may also be provided by reducing the wall thickness of the delivery container in one or more bending lines arranged at relevant locations in the delivery container. In one embodiment the bending lines may have the same depths, i.e. the wall thickness are the same for all bending lines, and/or have the same cutting angle, e.g. resembling a V, however a person skilled in the art will understand that the wall thickness and/or cutting angles of said bending lines may vary in order to adjust the required bending force of the compression zones. Furthermore, the extension and/or shape of the bending lines may vary, and may in one embodiment extend from the bottom of the delivery container to the top, i.e. in the complete height of the delivery container, and in another embodiment extend only in a part of the delivery container, be circular, triangular etc.

Alternatively, the compression zones may be provided by providing reinforcement ribs at the inside and/or outside of the delivery container. Said reinforcement ribs may have any desired shape and location and may accordingly be lines, be circular, be a section of a circle, have polygonal shape, etc.

The one or more compression zones of the delivery container may also be obtained by providing a delivery container made of differed kinds of material, and wherein the respective materials have a different harnesses, such that said the delivery container can be easier deformed in certain areas than in others.

Thus, the compression zones may be providing in different ways, e.g. using one or more of the possibilities discussed above, be placed symmetrically or asymmetrically on the delivery container, etc. however a person skilled in the art will understand that said compression zones may also be obtained in other ways, the only requirement being that a controlled compression of the delivery container is provided.

In order to ensure that the enema device according to the invention can be used by patients/users having week fingers, the delivery container may in an advantageously embodiment be arranged such that is may be fully compressed by a force of less than about 150 N, preferably less than 130 N, and even more preferred by a force less than 110 N. However, in order to prevent the delivery container from collapsing to early, i.e. during the handling of the enema device before the administration procedure is initiated, it is preferred that that a compression force of at least 30 N has to be applied before the delivery container start collapsing/compressing.

However, it is further preferred that the delivery container is arranged for compressing when a compression force of not more than 50 N is applied to the delivery container, e.g. the two longer sides by the palm and fingers. The desired forces used to compress the delivery container may e.g. be obtained by using special materials, adjusting the wall thickness of the delivery container, using the compression zones, etc.

In a preferred embodiment the delivery container is arranged for expelling at least 80-vol % of the enema accommodated in the delivery container, preferably at least 90 vol % and even more preferred substantially the entire content, when the delivery container is fully compressed or at least when the user cannot compress the delivery container further during the administration procedure.

In a preferred embodiment the delivery container is arranged for accommodating at least an effective dosage of enema, preferably slightly more. Within the context of the present invention the term "an effective dosage of enema" means the amount of enema which is required and/or sufficient for stimulating stool evacuation in the patient. Even though an effective dosage is individual, among others depending on the age of patient (e.g. child vs. adult) administration of enemas is well known in the art, and a person skilled in the art will have no problem of establishing an effective dosage of enema.

In one embodiment, the delivery container is arranged for accommodating at least about 90 ml of enema, and preferably at least about 130 ml which is slightly more than a conventional enema dosage for most adults. As the required amount of enema is individual, the enema device may in some preferred embodiments accommodate about 150 ml or even up to 250 ml, however the dimensions of said enema device may be adjusted to accommodate a higher or lower amount of enema, within the content of the present invention.

Using an enema device arranged for accommodating an effective dosage of enema, ensures that the user can administer a full and effective dosage of enema, without having to reload the device, and without having to worry about air being mixed with the enema. Accordingly, the patient/user can release the pressure on the delivery container as many times as desired, and the administration of the enema can take as long as the patient need or require without compromising the function of the enema device according to the invention, whereby a high patient compliance is provided.

Thereby is provided an enema device which is highly suitable for self-administration, as the effort required to expel the enema liquid is significantly reduced compared to the known enema devices.

In order to ensure that the enema is administered with a relatively high patient compliance, the enema device according to the invention is arranged for being connected to an applicator nozzle that preferably is arranged for alleviating the physical discomfort and pain that the patient may expire during insertion of the applicator nozzle. Said applicator nozzle is in fluid communicating with the delivery container, such that said enema can be expelled via an outlet in the applicator nozzle. As the applicator nozzle is inserted into the rectum of the patient, it is preferred that said applicator nozzle is releasably connected to the enema device, in order to allow said applicator nozzle to be either cleaned or discharged.

In order to facilitate refilling and re-use of the enema device according to the invention, it is preferred that the enema device can be restored to an initial position, i.e. a position where the enema device is ready for a new enema administration procedure. It is in this respect preferred, that the delivery container is arranged for being opened and closed, in order to allow an easy refilling of said container with enema. It is in this respect preferred that the enema device comprises a closure member comprising a first closure part arranged for being attached to the delivery container, and a second closure part arranged for being separating from or connected to, the first closure parts, respectively opening and/or closing the delivery container.

Such closure member are known in the art and includes threaded closure member, snap-fit closure member, closable lids, etc. It is however preferred that the closure member is a hinged closable lids, as this provides a simple embodiment in which it is ensured that the parts of the closure member cannot be misplaced. A fluid tight seal is preferably provided between the first and second closure parts when the closure member is in a closed position, in order to prevent leakage of the enema.

In a simple embodiment the non-return valve is incorporated into the closure member, whereby said valve can be reused, even if the applicator nozzle is discharged.

It is further preferred that when the second closure part is removed/separated from the first closure part, a first opening is provided into the delivery container, and that said first opening has a size that allows an easy manual refilling of enema into the delivery container. It is accordingly preferred that said first opening constitutes at least 50% of a cross-section taken at the top section of the delivery container, preferably at least 60%, and even more preferred at least 80% of the cross-section taken at the top section of the delivery container. A relatively large opening into the delivery container will also allow the inside of the delivery container to be effectively cleaned and dried between different enema administrations, thereby providing a more hygienic enema device than hitherto known.

The second closure part may in a preferred embodiment comprise a coupling unit arranged for releasably connecting the applicator nozzle to the enema device and for providing a fluid communication between the applicator nozzle and the delivery container. Accordingly, the second closure part may comprise a second opening in fluid communication with the delivery container via the first opening, such that enema in the delivery container can be expelled via said applicator nozzle.

The closure member may in one embodiment be made of a rigid material, e.g. polypropylene or polyvinyl chloride, thereby not only ensuring that the closure member can be opened/closed but also that the applicator nozzle easily can be releasable attached to the closure member. Said applicator nozzle may be attached to the closure member in any conventional and convenient way, e.g. using a snap-fit, or the like, however in a preferred embodiment the applicator nozzle comprises a tube defining an inlet at one end, and wherein said tube can be sealingly inserted into the second opening.

In order to ensure a fluid tight seal between the closure member and the deliver container, said closure member may preferably be attached to the delivery container via an intermediate member, preferably matching the oval shape of the top section of the delivery container. Said intermediate member is preferably also made of a rigid material, and may be integrated with the second closuring part, and may be attached to the top section of the delivery container via an adhesive or the like.

The term “enema” covers any liquid, which is capable of promoting bowel movement when introduced into the rectum and colon, such as an enema liquid. Examples of enema liquids include water; hypertonic aqueous salt solutions; solutions or suspensions of cathartic agents, such as bisacodyl or phenolphthalein; and mineral oil. Other liquids capable of promoting bowel movements are well known in the art, and are also contemplated within the scope of the present invention. It is however preferred that the enema has a low viscosity that ensures that the enema easily can be distributed evenly in the colon, e.g. a viscosity corresponding to or being close to the viscosity of water. Gels or liquids having a high viscosity i.e. they cannot flow easily, is accordingly not preferred.

The applicator nozzle may have any shape so long as the nozzle is able to perform the function of administrating the enema to the patient’s rectum and/or colon. In a preferred embodiment the applicator nozzle has a mainly frustoconical shape whose outside diameter progressively decreases from it’s proximal end to it’s distal as said shape automatically will ensure a tight fit with the anal opening.

The applicator nozzle can furthermore be modified in size, shape and possibly other physical properties such as flexibility, rigidity and pliancy to become a plug that accommodates forming a sealing fit with the anal opening. For example, if at least the nozzle is somewhat pliable, it will conform to the shape of the patient’s rectum and aid in alleviating the physical discomfort and pain that the patient may expire during insertion of the nozzle.

The nozzle can furthermore be provided with e.g. a pointed blunt tip in order to further reduce said discomfort, a lubricant or an activated hydrophilic coating in order to aid the insertion of the nozzle in the rectum by reducing frictional force.

The applicator nozzle can preferably be disposable in order to reduce contamination of the surroundings e.g. by providing a nozzle, which can be flushed down the toilet after use. This will also make the device more convenient and hygienic in use, however said nozzle may also, if desired, be arranged for being reused after being cleaned and/or sterilised. In any case it is preferred that the applicator nozzle is made of a hypoallergenic material that is non-reactive with the patient's tissue.

The enema device according to the present invention has a simple and user-friendly design, making it extremely easy to operate with a single hand ensuring that the device can be unassistedly used in privacy. When a new administration proceedings is to be initiated, the user can easily refill the delivery container with enema, close the closure member and connect an applicator nozzle to the delivery container, whereby the enema device according to the invention is ready for the next enema administration.

The user can then placed the enema device in a cupped hand, and apply pressure to the sides of the delivery container. As air, faeces or liquid cannot be drawn into the delivery container, the user can reduce the pressure, e.g. simply holding the enema device in place, and reapply pressure at the users convenience until the delivery container is sufficiently compressed e.g. completely, and the desired dosage of enema has been delivered to the colon.

After the administration procedure is completed the user can e.g. discharge the applicator nozzle, open the closure member whereby air will enter the delivery container and return said container to it's original shape. The relatively large first opening into the delivery container will further ensure that the delivery container can be cleaned and dried between the administration procedures.

In a preferred embodiment the delivery container has a height of about 7 cm, and the cross-section of the bottom-section has a minor axis of 2.50 cm and a major axis of 3.75 cm, the cross-section of the top section has a minor axis of 2.00 cm and a major axis of 3.00 cm, and the first opening is a circle having a radius of 1.75 cm.

Figure 2B:
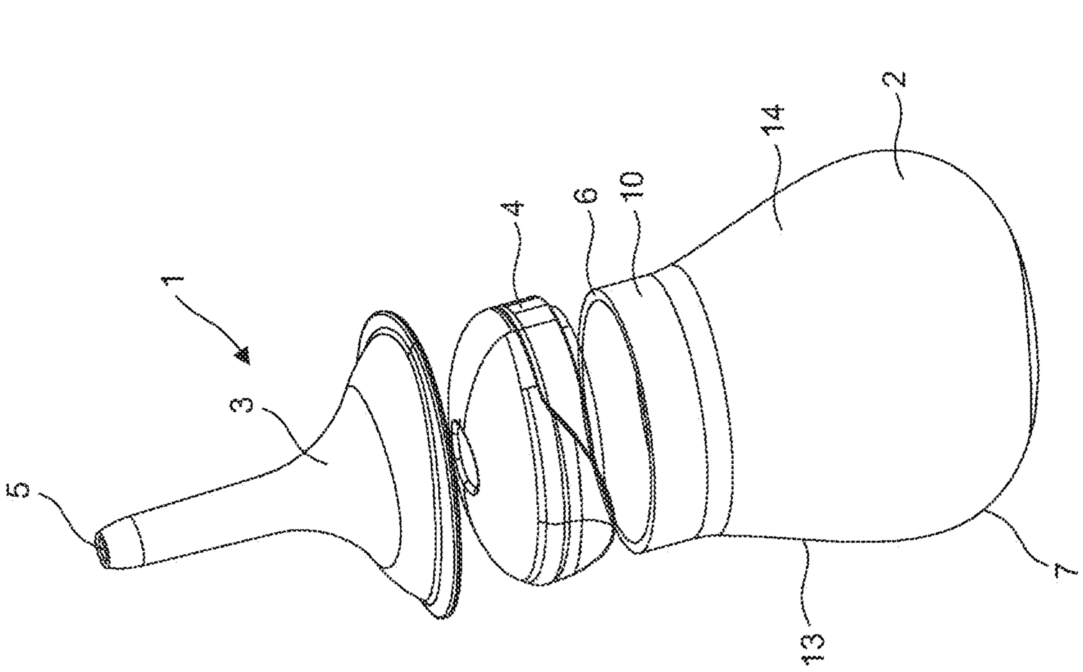
Figure 2A:
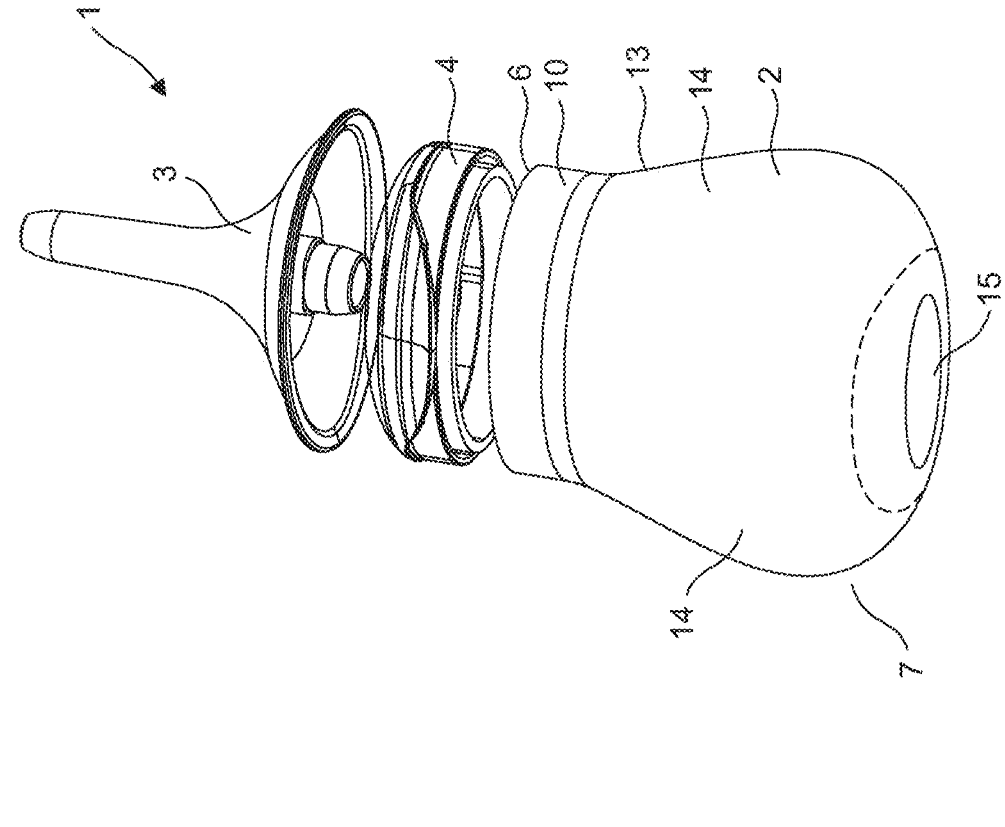
Figure 3A:
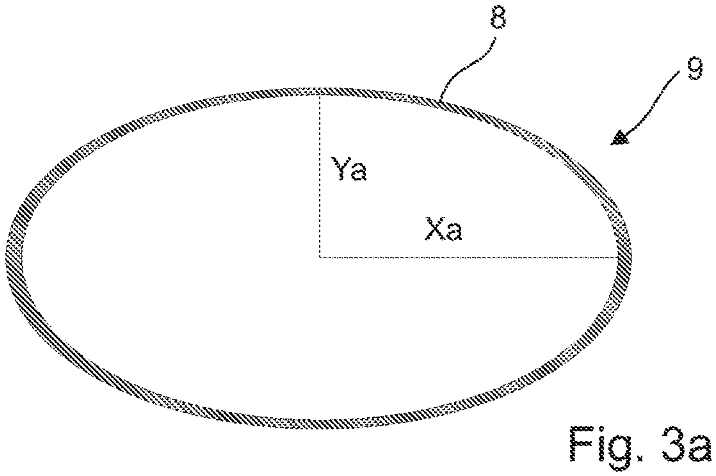
Figure 3B:
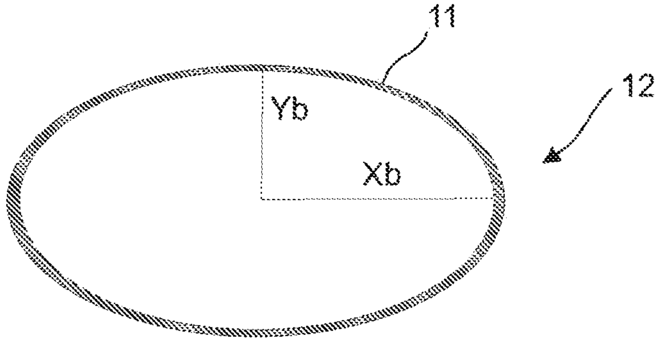
Figure 4A:
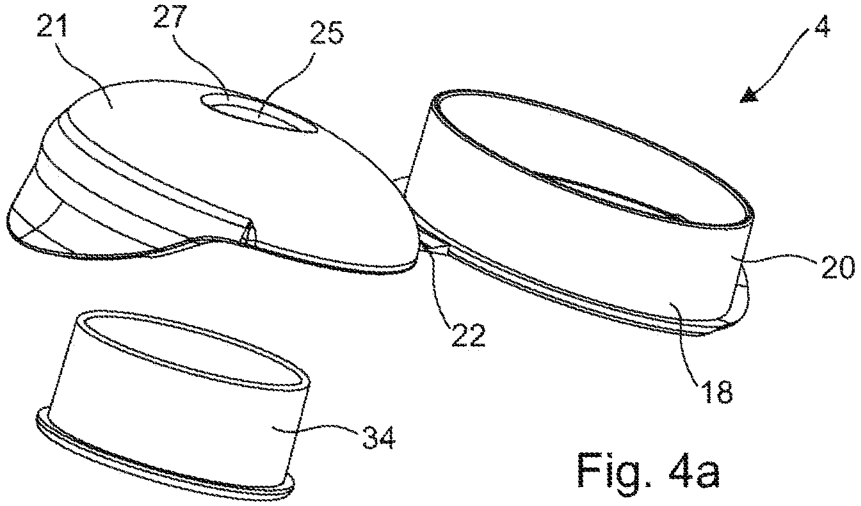
Figure 4B:
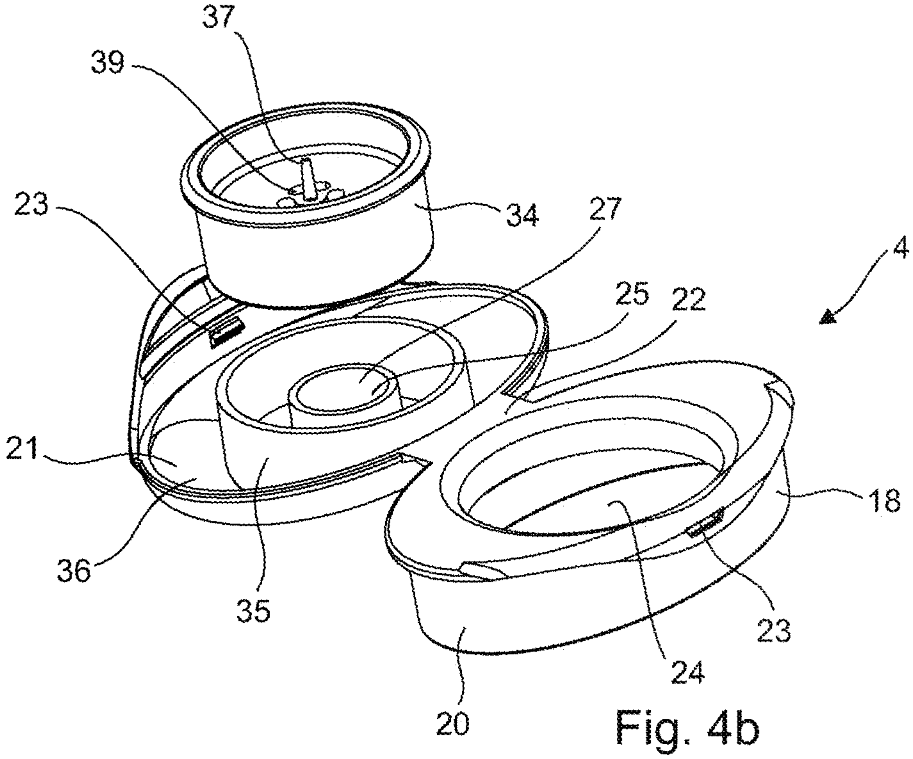
Figure 5:
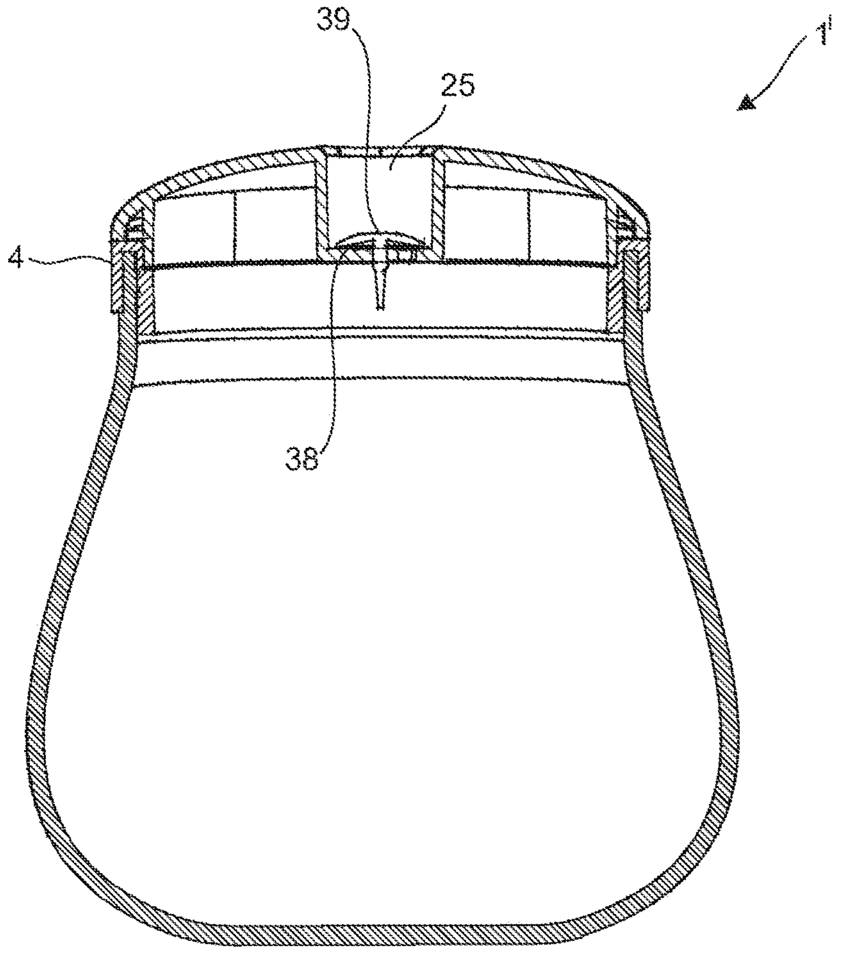
Figure 6:
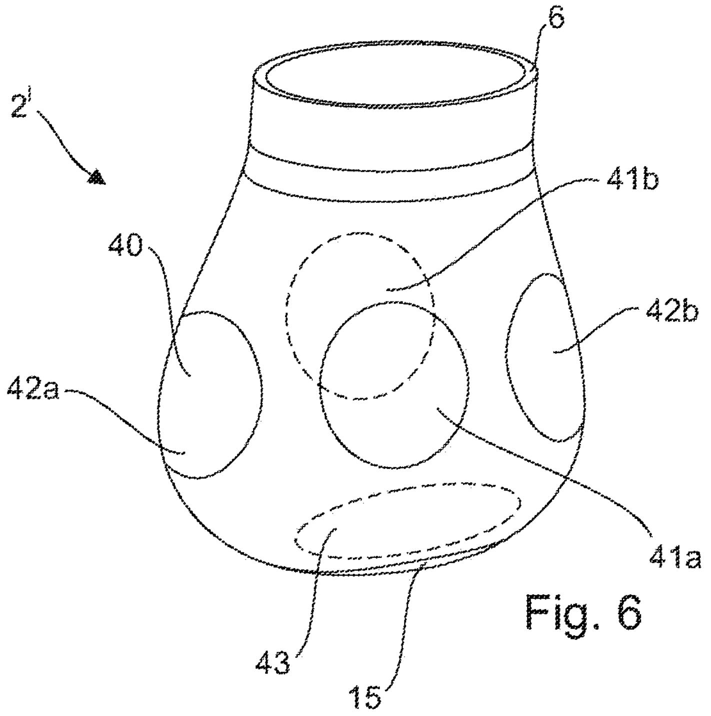
Figure 7:
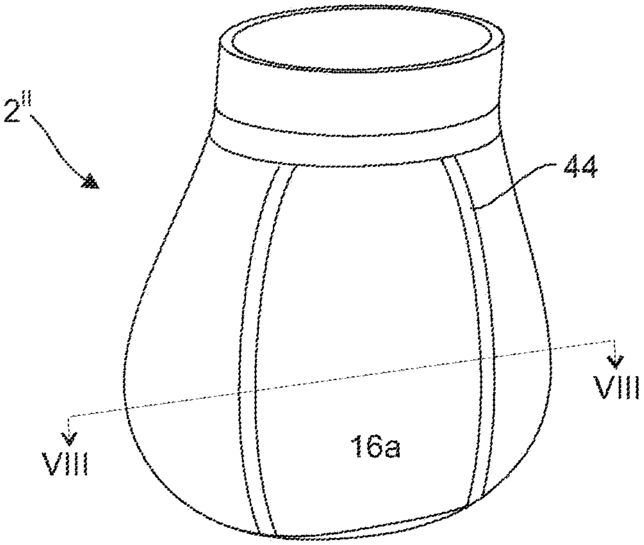
Figure 8A:
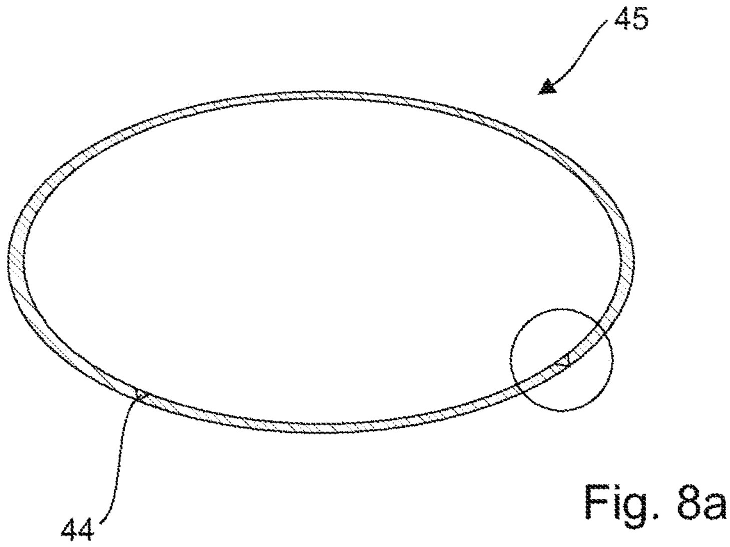
Figure 8B:
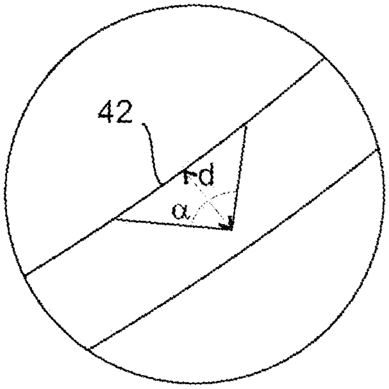

The invention will be explained in greater detail below, describing only exemplary embodiments of the enema device with reference to the drawing, in which FIG. 1 shows a perspective view of an enema device according to the present invention with a first embodiment of a delivery container, FIGS. 2*a*-2*b* show exploded perspective views of the enema device shown in FIG. 1 seen from the bottom and top, respectively, FIGS. 3*a*-3*b* respectively illustrates the cross-section of the delivery container taken along the lines IIIa-IIIa and IIIb-IIIb in FIG. 1, FIGS. 4*a*-4*b*. show exploded perspective views of the closure member seen from the top and bottom, respectively, FIG. 5 shows a cross-sectional view of a second embodiment of the enema device, FIG. 6 shows a second embodiment of a delivery container according to the invention, FIG. 7 shows a cross s section of a third embodiment of a delivery container according to the invention, FIG. 8*a* shows a cross section of the delivery container taken along the lines VIII-VIII in FIG. 7, and FIG. 8*b* shows the enlarged section C of FIG. 8*a*.

FIG. 1. is a schematic view of a first embodiment of the enema device 1 according to the invention, and FIG. 2 is the same in an exploded view. Said device consist basically of an enema delivery container 2, arranged as a hand held pump having a cross-section that is substantially oval, an applicator nozzle 3 and a closure member 4. The applicator nozzle 3 has an exit opening 5 through which the enema can be expelled when pressure is applied to the delivery container 2.

In the embodiment shown in FIG. 1 and FIG. 2 the delivery container 2 comprises an opening 6, a bottom section 7 with a first cross-section 8 in the shape of a first oval 9, and a top section 10 with a second cross-section 11 in the shape of a second oval 12. FIG. 3*a* shows the first oval 9 taken along the lines IIIa-IIIa in FIG. 1, and FIG. 3*b* shows the second oval 12 taken along the lines IIIb-IIIb of FIG. 1.

The major axis Xa and the minor axis Ya of said first oval 9 is larger than the major axis Xb and the minor axis Yb of the second oval 12, and the bottom section 7 tapers towards the top section 10 such that a smooth transition 13 between the two sections 7,10 is provided, whereby the delivery container 2 obtains the shape of an elongated bulb 14 as shown in e.g. FIG. 1, having a base 15 allowing the enema device 1 to rest on a surface (not shown), two longer curved sides 16*a*, 16*b*, and two shorter curved sides 17*a*, 17*b*.

The base 15 further ensures that enema device 1 may stand in an upright position both when said container 2 is filled with enema, and during handling of said device 1, e.g. when closing the closure member 4 and connection of the applicator nozzle 3.

The delivery container 2 has a cross-section in the shape of an oval 9,12 irrespectively of where said cross-section is made in the delivery container 2, i.e. the oval shape continues in the complete height H of the delivery container 2. The oval cross-section(s) 8,11 and the elongated bulb-shape 14 of the delivery container 2 ensures that it is easier for the user to apply pressure to e.g. the sides 16*a*, 16*b* of the delivery container 2. The user will intuitively place/rest the delivery container 2 with the bottom in the users palm, whereby it will be easy to compress the container 2 by applying pressure to the two longer curved sides 16*a*, 16*b* of the delivery container 2 using both the finger and the palm, e.g. the thenar muscles at the base of the thumb. Thus, the use of an oval cross-section 8, 11 will provide a pleasant fit in the hand of the user as well as reducing the compression force required to compress the container 2. A person skilled in the art will understand that the user may apply pressure on the delivery container 2 in a different manner if desired, e.g. having the palm of the hand resting against one of the two shorter curved sides 17*a*, 17*b* of the delivery container 2.

FIGS. 4*a* and 4*b* show exploded perspective views of the closure member 4 seen from the top and bottom respectively. Said closure member 4 comprises a first closure part 18 arranged for being attached to the top 19 of the delivery container 2 via an intermediate part 20, and a second closure part 21 arranged for being separating from or connected to the first closure part 18 via a hinge member 22 and a click-fit connection 23. In this way the closure member 4 functions as a hinged closable lid, having the advantages that the second closure part 21 cannot be misplaced during use. Furthermore, the click-fit connection 23 ensures that the user knows when the closure member 4 is closed i.e. when a fluid tight seal is provided between the first and second closure parts 18,21, in order to prevent leakage of the enema. A person skilled in the art will understand that the shown closure member 4 is one of many possibilities of providing an opening 6 into the delivery container 2, and that others, e.g. threaded closure members, also are contemplated within the scope of the present invention. Sealing rings (not shown) or the like, may be used, if necessary, in order to ensure that the liquid tight seal is obtained.

The intermediate part 20 is permanently and securely connected to the inside of the top 19 of the delivery container 2, e.g. using a glue, welding or similar means, thereby providing a reliable and durable construction, in which the closing member 4 in a simple manner can be open and closed. However, the intermediate part may also be connected with the delivery container using an overmoulding process, a 2K injection moulding process, and/or similar a process, the only requirement being that the closure member 4 is securely connected to the delivery container 2.

In order to ensure that the enema can be expelled from the delivery container 2, the first closure part 18 comprises a first opening 24 and the second closure part 21 comprises a second opening 25, together a which provides fluid communication between the delivery container 2 and the exit opening 5 of the applicator nozzle 3 when said nozzle is attached to the closure member 4.

In the embodiment shown in the figures, the applicator nozzle 3 is removable connected to the closure member 4 by means of a coupling unit 26. This is best seen in FIG. 2. Said coupling unit ensures that the applicator nozzle 3 can be removed after use and then be either cleaned, sterilised or simply discarded.

The coupling unit 26 consist of a female coupling part 27, placed in the second coupling part 21 and extends into the second opening 25, and is arranged for engaging a male coupling part 28 placed on the applicator nozzle 3. In the embodiment shown the male coupling part 28 is a short flexible tube 29, extending via an inner tube 30 in the applicator nozzle 3, to the exit opening 5. The female coupling part 27 is made of a rigid material, such that a liquid tight seal is provided between the two parts 27, 28 and when they are engaging. The male coupling part 28 has a tapered end 31 for facilitating a simple engagement with the female part 27 when the male coupling part 28 is inserted into and retracted from the female coupling part 27.

The applicator nozzle 3 further comprises an annular, substantially frustoconical extension 32, which not only provides a comfortable design for the user and a tight fit with the anal opening during the administration proceedings, but also a stop for limiting the extension of the male coupling part 28 into the female coupling part 27 when the two parts are connected. Thereby is an especially simple and inexpensive design of the enema device 1 according to the invention obtained.

In the embodiment shown, the applicator nozzle 3 has a single exit opening 5 at its distal end 33. In a variant, several exit openings may be formed at the distal end 33 of the applicator nozzle, 3 including one or more orifices (not shown) located at offset locations along the surface of the distal end of the applicator nozzle. This offset configuration for the location of the exit openings may be particularly desirable where the user's rectum or colon is inflamed or otherwise sensitive to contact by a pressurized stream of fluid.

As is best seen in FIG. 4*b* a cylindrical valve seat 34 for a non-return valve (not shown) is sealingly fitted into the second closure part 21 via a corresponding cylindrical rim 35 arranged on the inside 36 of said second part 21, such that backflow of fluid e.g. air, liquid and faeces from the colon and/or rectum into the enema device effectively is prevented at the second opening if/when the patient/user released the compression force on the delivery container. The valve seat 34 comprises three openings 37 which may be closed with e.g. an umbrella valve as the non-return valve.

The closure member 4 is preferably made of a rigid material, e.g. polypropylene or polyvinyl chloride, thereby not only ensuring that the closure member 4 can be opened/closed but also that the applicator nozzle 3 easily can be releasable attached to the second closure part. As is best seen in fig. FIG. 4*b*, the first opening 24 is relatively large, i.e. it both allow an easy manual refilling of enema into the delivery container 2, and that the inside of the delivery container 2 can cleaned between be and dried different enema administrations. In the embodiment shown, the first opening 24 constitutes an area of about 60% of the area A of the cross-section 11 taken at the top section 10 of the delivery container 2, however a person skilled in the art will understand that said size may vary if desired.

FIG. 5 shows a cross-sectional view of a second embodiment of the enema device 1'. Said embodiment corresponds to the embodiment shown in FIG. 1-3 with the difference that the closure member 4' is modified. Thus, for like parts the same reference number is used. In the second embodiment 1', the closure member 4' does not comprise a valve seat 34, instead the second opening 25 of the second closure part 21 comprises a base 38 having openings 37, to which a non-return umbrella valve 39 is fitted.

FIG. 6 shows a second embodiment of a delivery container 2' for use in an enema device 1 according to the invention. Said embodiment 2' corresponds to the first embodiment of the delivery container 2, with the modification that a number of compression zones 40 are provided in the delivery container 2'. Accordingly, the same reference numbers are used for like parts. The compression zones 40 are in the embodiment shown defined by two opposing circular areas 41*a*, 41*b* on the two longer curved sides 16*a*, 16*b* of the delivery container 2', two opposing circular areas 42*a*, 42*b* on the two smaller sides 17*a*, 17*b* of the delivery container 2', and a single circular area 43 at the base 15 of the delivery container 2'. The top section 10 of the delivery container will be reinforced by the intermediate section 20 from the closure member 4, and will accordingly not be able to be compressed to a significant degree. However, the different circular compression areas 40 may have different harnesses e.g. thicknesses and accordingly be arranged to bend/yield when different forces are applied to said areas 40. For instance the force needed to compress the delivery container at the circular area 43 at the base 15, may be lager than forces needed to compress the delivery container at the two opposing circular areas 42*a*, 42*b* on the two smaller sides 17*a*, 17*b* of the delivery container 2', and the force needed to compress the delivery container at the two opposing circular areas 41*a*, 41*b* on the two longer curved sides 16*a*, 16*b* may be the lowest. In this way it is ensured that when a user provides pressure to the delivery container 2', said container will collapse/compress in such a way that substantially the entire content of the enema device is expelled.

The compressions areas may be provided by adjusting the wall thickness of the delivery container in the compression areas 40, e.g. such that the wall thickness in compression areas 41*a*, 41*b* on the longer sides is the lowest, and the compression area 43 at the base is the highest. Alternatively, the different compressions areas 40 may be made of different materials having different hardness, have different curvatures, e.g. double curvatures and the like.

A person skilled in the art will understand that more or fewer compression areas 40 may be provided, each having different hardness/wall thickness. Said compression areas need not be but may circular, have other desired shapes, e.g. be triangular, etc. Furthermore, one or more of said compression areas may be arranged for not collapsing at all, even if a large compression force is applied to said area.

FIG. 7 shows a third embodiment of the delivery container 2" according to the invention, in which the compression zones 40 are provided by reducing the wall thickness X of the delivery container in two bending lines 44 arranged at one of the long curved surfaces 16*a*, a cross section 45 taken along the lines VIII-VIII is shown in FIG. 8*a*. The bending lines are shaped as a V, see enlarged view of a bending line in FIG. 8*b*, have the same cutting angle α, and the same depths d, i.e. the characteristics of the bending lines are the same for the two bending lines 44. However a person skilled in the art will understand that said bending lines and/or the shape of the bending line and/or the depth (wall thickness) and/or cutting angles of said bending lines may vary in order to adjust the required bending force of the compression zones. Furthermore, the number of bending lines and/or placement of said bending lines may be adjusted.

Alternatively, the compression zones may be provided by providing reinforcement ribs (not shown) at the inside and/or outside of the delivery container. Said reinforcement ribs may have any desired shape and location and may accordingly be lines, be circular, be a section of a circle, have polygonal shape, etc.

When an enema is to be administered an enema, e.g. saline or tap water, is filled into the delivery container 2,2',2" via the first opening 24, then closing the closure member 4 and place an applicator nozzle 3 on said closure member 4 via the coupling unit 26. In order to prevent air from being entered into the colon, it is preferred that the delivery container 2,2',2" is completely or at least substantially filled with said enema.

In order to initiate the administration procedure, the applicator nozzle 3 is then placed in the patient's anal opening and it is ensured that the nozzle 3 provides a tight fit with the opening.

Compression force is then applied to the delivery container 2,2',2" by squeezing the delivery container. The enema is allowed to flow through the first 24 and second 25 opening, into the tube 30 of the applicator nozzle 3 and out of the exit opening 5, resulting injected into the rectum and colon.

When the user during the administration procedure releases the compression force on the delivery container 2,2',2", said container will remain compresses as the non-return valve 39 will prevent fluid from entering the delivery container. Furthermore, since the non-return valve 39 effectively prevents air from being mixed with the enema, air cannot be administered into the patients colon and unnecessary discomfort caused by distending of the colon by air, is effectively prevented.

After each squeezing and subsequent release action the delivery container 2,2',2" will be more and more compressed, gradually reducing the size of said container, allowing the user to fell when the desired dosage of enema has been administered, or the entire enema content has been expelled from the device.

After the enema is administrated into the rectum and/or colon the enema device 1 is removed from the anal opening, and the applicator nozzle 3 can be detached from the delivery container 2,2',2" and either be discarded or cleaned for later use. The second closure member 21 can then be released from the first closure member 18, allowing the inside of the delivery container 2,2',2" to be cleaned and/or dried via the first opening 24. When a new administration procedure is to be initiated, the enema device 1 can be restored to it's initial position by refilling the delivery container 2,2',2" with enema as already described.

Since the enema device 1 according to the invention are relatively small and intended for use with a single hand, it can used equally well for both home-administrations of enema or for the use in medical or hospital facilities where larger irrigations/enema devices are too troublesome and complicated to use.

Modifications and combinations of the above principles and designs are foreseen within the scope of the present invention.

What is claimed is:

1. An enema device comprising a flexible delivery container arranged for accommodating an enema and an applicator nozzle for dispersing the enema, and wherein the delivery container is arranged as a hand held pump and for remaining in an at least partly compressed configuration when a user releases pressure on said delivery container during use, wherein the enema device comprises a closure member, comprising a first closure part arranged for being attached to the delivery container, and a second closure part arranged for being separated from or connected to the first closure part, and wherein the second closure part comprises a female coupling part arranged for releasably connecting a male coupling part of the applicator nozzle to the enema device and for providing a fluid communication between the applicator nozzle and the delivery container.

2. The enema device according to claim 1, wherein the closure member is a hinged lid.

3. The enema device according to claim 1, wherein a first opening is provided into the delivery container when the second closure part is separated from the first closure part, and wherein said first opening constitutes at least 50% of a cross-section taken at the top section of the delivery container.

4. A delivery container as defined in claim 1, arranged for being connected to an application nozzle via a closure member.

5. The enema device according to claim 1, wherein a cross-section of said delivery container has the shape of an oval.

6. The enema device according to claim 1, wherein the delivery container comprises a bottom section with a first cross-section in the shape of an oval, and a top section with a second cross-section in the shape of an oval, and wherein the minor and/or the major axis of the first cross-section is larger than the respective minor and/or the major axis of the second cross-section.

7. The enema device according to claim 6, wherein the ratio of the minor axis to the major axis of said oval is ⅔ or lower.

8. The enema device according to claim 6, wherein the bottom section tapers towards the top section, thereby providing a smooth transition between the two sections.

9. The enema device according to claim 1, wherein the enema device comprises a non-return valve arranged for preventing fluids from being drawn into the delivery container during operation.

10. The enema device according to claim 1, wherein the delivery container is made of a resilient deformable material with a memory.

11. The enema device according to claim 1, wherein the delivery container is arranged for expelling at least 80-vol % of the enema accommodated in the delivery container.

12. The enema device according to claim 1, wherein the delivery container comprises one or more compression zones arranged for providing a controlled compression of said delivery container.

13. The enema device according to claim 12, wherein the one or more compression zones constitute less than 50% of the surface area of the delivery container.

14. The enema device according to claim 12, wherein the one or more compression zones are provided by adjusting the wall thickness of the delivery container in one or more compression zones.

15. The enema device according to claim 12, wherein the one or more compression zones are provided by reducing the wall thickness of the delivery container in one or more bending lines.

16. The enema device according to claim 12, wherein the one or more compression zones are provided by providing reinforcement ribs at the inside and/or outside of the delivery container.

17. The enema device according to claim 12, wherein the delivery container is made of more than one material, and wherein the respective materials have a different hardness in order to define the one or more compression zones.

18. The enema device according to claim 1, wherein the delivery container is arranged for being fully compressed by a force of less than about 150 N.

19. The enema device according to claim 1, wherein the delivery container is arranged such that said delivery container will not be compressed before a force of between about 30 N and about 50 N is applied to the sides of said delivery container.

20. The enema device according to claim 1, wherein the delivery container is arranged for accommodating at least about 90 ml of enema.

21. A method of administering an enema using the enema device according to claim 1, wherein said method comprises the step of: placing the applicator nozzle in a patient's anal opening; squeezing the delivery container thereby allowing the enema to flow out of the applicator nozzle and into the rectum and colon of the patient; alternating applying pressure and releasing said pressure from the delivery container, until the desired dosage of enema or the entire enema content has been expelled from the delivery container; removing the applicator nozzle from the patient's anal opening; wherein the delivery container will remain in an at least partly compressed configuration when the user releases the pressure on said delivery container.

22. A method according to claim 21, wherein an effective dosage of enema can be administered without required reloading of the delivery container.

23. A method according to claim 21, wherein air and liquid is prevented from being drawn into the delivery container when the user releases the pressure on the delivery container.

* * * * *